US00PP34175P2

(12) United States Plant Patent
Nguyen

(10) Patent No.: US PP34,175 P2
(45) Date of Patent: Apr. 26, 2022

(54) ***ANGELONIA* PLANT NAMED 'SAIANG001'**

(50) Latin Name: *Angelonia angustifolia*
Varietal Denomination: SAIANG001

(71) Applicant: Sakata Seed America, Inc., Morgan Hill, CA (US)

(72) Inventor: Phuong N. Nguyen, Thousand Oaks, CA (US)

(73) Assignee: Sakata Seed America, Inc., Morgan Hill, CA (US)

( * ) Notice: Subject to any disclaimer, the term of this patent is extended or adjusted under 35 U.S.C. 154(b) by 0 days.

(21) Appl. No.: 17/495,106

(22) Filed: Oct. 6, 2021

(51) Int. Cl.
*A01H 5/02* (2018.01)
*A01H 6/68* (2018.01)

(52) U.S. Cl.
USPC ..... Plt./404

(58) Field of Classification Search
USPC ..... Plt./404
See application file for complete search history.

*Primary Examiner* — Susan McCormick Ewoldt
(74) *Attorney, Agent, or Firm* — Weatherly IP Solutions, LLC; Barbara Campbell

(57) ABSTRACT

An *Angelonia* plant particularly distinguished by having white flowers, strong stems, and an upright plant habit, is disclosed.

2 Drawing Sheets

Genus and species: *Angelonia angustifolia.*
Variety denomination: 'SAIANG001'.

BACKGROUND OF THE NEW PLANT

The present invention relates to a new and distinct cultivar of *Angelonia* plant botanically known as *Angelonia angustifolia* and hereinafter referred to by the cultivar name 'SAIANG001'. The new cultivar originated from a controlled breeding program in Guadalupe, Calif. during June 2013. The objective of the breeding program was to develop *Angelonia* cultivars having strong stems, white flower color, and an upright plant habit.

The new *Angelonia* cultivar is the result of cross-pollination between the female (seed) parent, the proprietary *Angelonia angustifolia* breeding selection '5327-3' (unpatented), characterized by its light-purple colored flowers, medium-green colored foliage, and moderately vigorous, upright growth habit, and the male (pollen) parent, the proprietary *Angelonia angustifolia* breeding selection '5732-2' (unpatented), characterized by its light-pink colored flowers, medium-green colored foliage, and moderately-vigorous, upright growth habit. The new cultivar was selected as a single flowering plant within the progeny of the above stated cross-pollination during May 2014 in a controlled environment in Guadalupe, Calif.

'SAIANG001' has been asexually reproduced since May 2014 by terminal stem cuttings in Guadalupe, Calif. The breeder has confirmed that 'SAIANG001' reproduces true to type with all of the characteristics, as herein described, firmly fixed and retained through successive generations of such asexual propagation via terminal stem cuttings.

SUMMARY

The following are the most outstanding and distinguishing characteristics of this new variety when grown under normal horticultural practices in Salinas, Calif.

1. White flowers;
2. Strong stems; and
3. An upright plant habit.

DESCRIPTION OF THE PHOTOGRAPHS

This *Angelonia* plant is illustrated by the accompanying photographs which show the plant's overall plant habit including form, foliage, and flowers. The photographs are of a plant 4.75-months from transplant into quart pots from rooted cuttings in Salinas, Calif. under greenhouse conditions. The colors shown are as true as can be reasonably obtained by conventional photographic procedures.

DESCRIPTION OF THE NEW VARIETY

Figure 1:
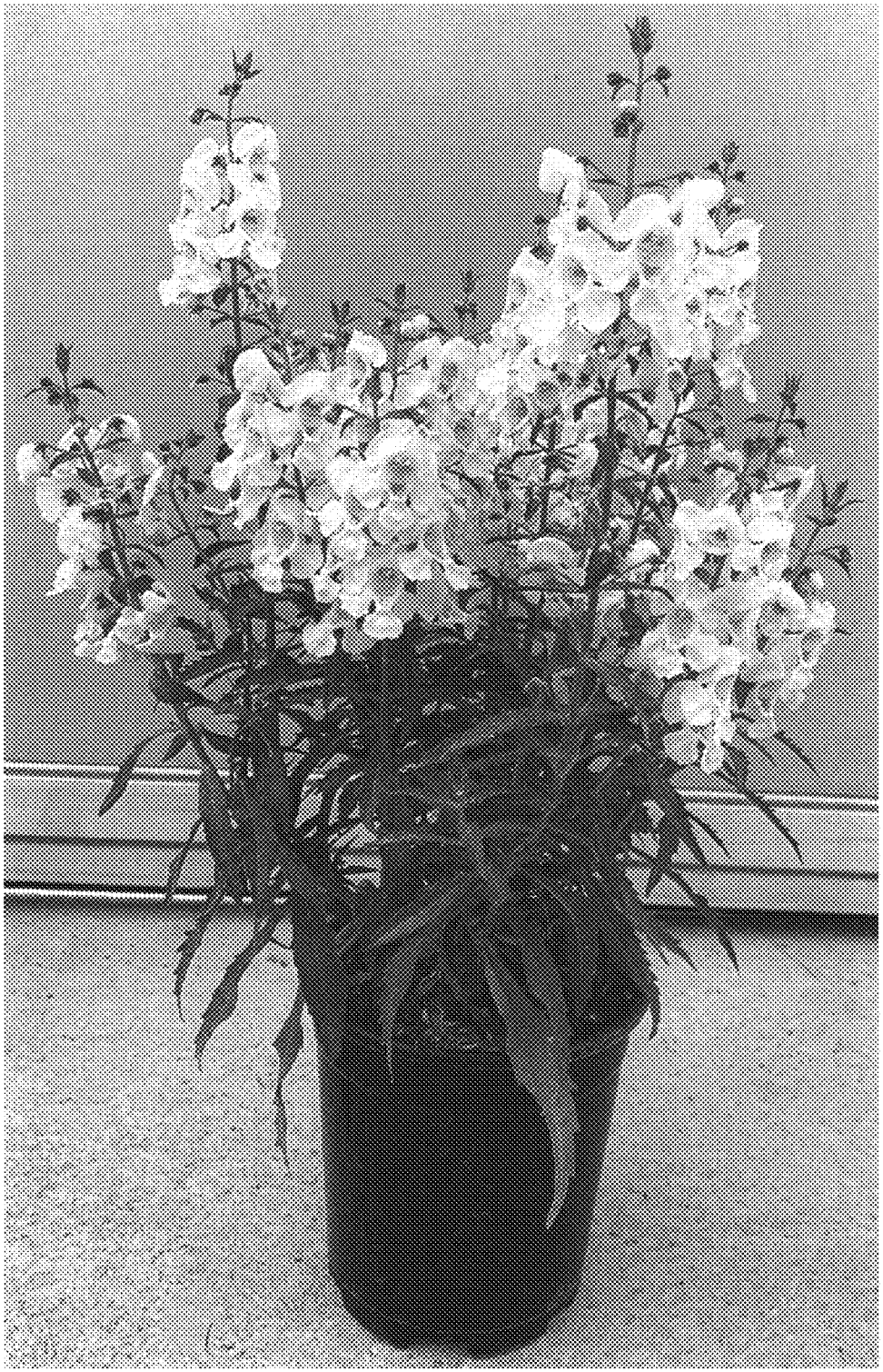
FIG. 1 shows the overall plant habit of the plant grown in a pot.
Figure 2:
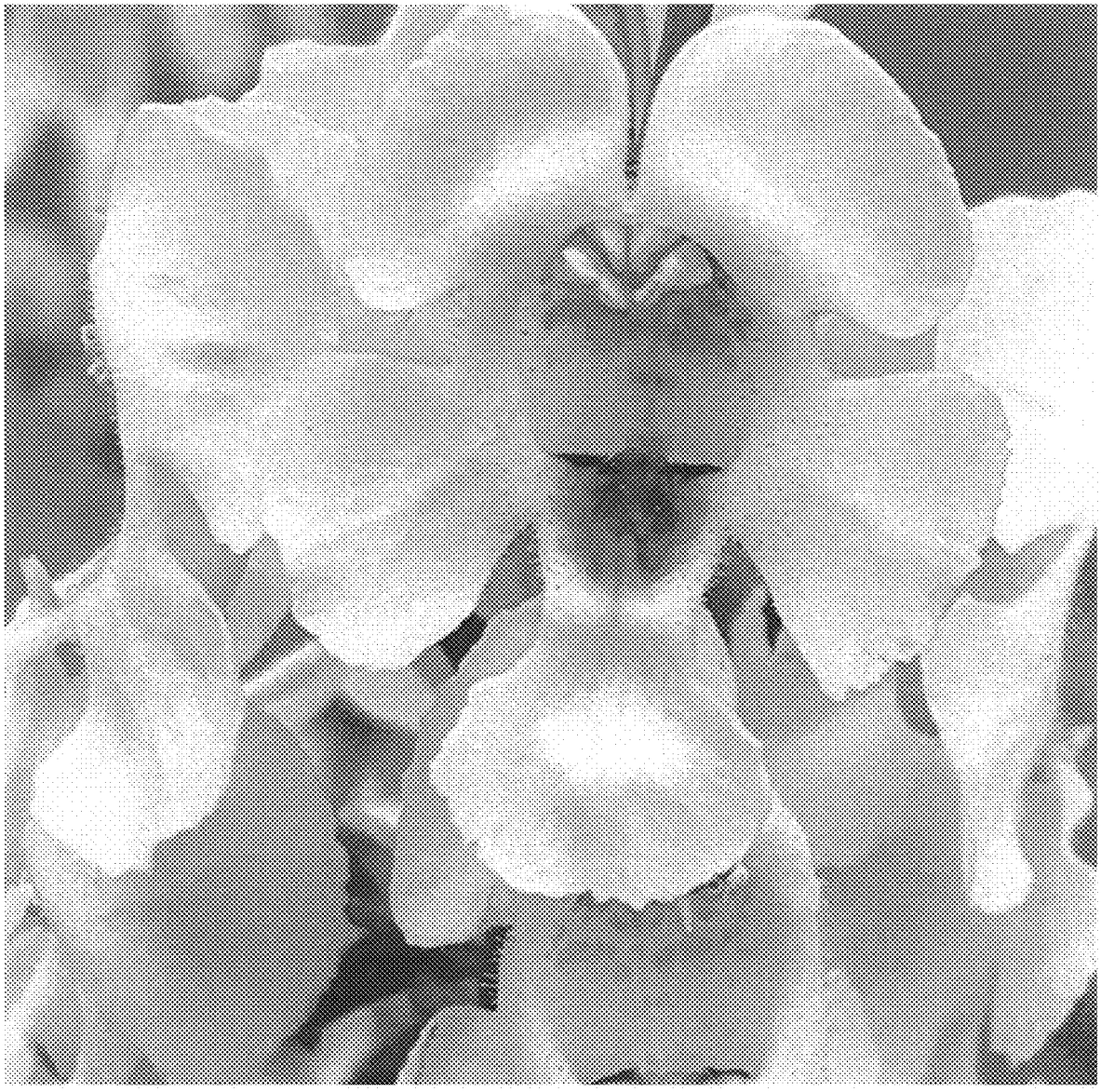
FIG. 2 shows a close-up of the mature flower of the plant.

The following traits and characteristics describe the new variety. Data obtained from plants grown 4.75-months from transplant into quart pots from rooted cuttings in Salinas, Calif., under greenhouse conditions. Color references are to The Royal Horticultural Society of London colour chart (R.H.S.), $6^{th}$ edition (2015). Anatomic labels are from *The Cambridge Illustrated Glossary of Botanical Terms*, by M. Hickey and C. King, Cambridge University Press.

Classification:
*Family.*—Plantaginaceae.
*Botanical.*—*Angelonia angustifolia.*
*Common.*—*Angelonia*; summer snapdragon.
*Designation.*—'SAIANG001'.

Parentage:
*Female.*—The proprietary '5327-3' (unpatented).
*Male.*—The proprietary '5732-2' (unpatented).

Growth: The terminal 1.0 to 1.5 inches of an actively growing stem was excised. The vegetative cuttings were propagated in five to six weeks. The base of the cuttings was dipped for 1 to 2 seconds in a 1:9 solution of DIP 'N GROW (1 solution:9 water) root inducing solution immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed. Rooted cuttings were transplanted and grown in plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow-release fertilizer containing 20% nitrogen, 10% phosphorus and 18% potassium. The typical average air temperature was 24 degrees Celsius.

Propagation:

*Type*.—Cutting; terminal stem.

*Time to initiate roots*.—Approximately 7 to 9 days.

*Time to produce a rooted cutting*.—Approximately 28 to 35 days.

*Root description*.—Fine, fibrous.

*Rooting habit*.—Freely branching.

Plant:

*Commercial crop time*.—Approximately 5 to 8 weeks from a rooted cutting to finish in a 10-cm pot.

*Growth habit and general appearance*.—Upright.

*Height from soil level to top of plant plane*.—Approximately 28.0 cm.

*Width*.—Approximately 20.0 cm.

*Branching habit*.—Freely branching.

*Quantity of main branches per plant*.—Approximately 2.

Branch:

*Shape*.—Square in cross section.

*Strength*.—Strong.

*Length*.—Approximately 23.0 cm from soil to start of inflorescences.

*Diameter*.—Approximately 5.0 mm.

*Length of central internode*.—Approximately 1.5 cm.

*Texture*.—Very slightly pubescent, RHS NN155D (White).

*Color of young and mature stems*.—RHS 144A (Strong Yellow Green).

Leaves:

*Quantity of leaves per main branch*.—Approximately 10 leaves prior to main branch splitting off.

*Fragrance*.—Absent.

*Form*.—Simple.

*Arrangement*.—Opposite.

*Aspect*.—Perpendicular or acute aspect to the stem.

*Shape*.—Lanceolate.

*Apex*.—Acuminate.

*Base*.—Attenuate.

*Margin*.—Serrate.

*Venation pattern*.—Pinnate.

*Venation color*.—Upper and lower surfaces: RHS 145C (Light Yellow Green) midvein.

*Length of mature leaf*.—Approximately 6.8 cm.

*Width of mature leaf*.—Approximately 1.4 cm.

*Texture of upper and lower surfaces*.—Very slight pubescence, RHS NN155D (White).

*Color of young foliage*.—Upper surface: Closest to but darker than RHS NN137A (Greyish Olive Green). Lower surface: Closest to but darker than RHS 147B (Moderate Yellow Green).

*Color of mature foliage*.—Upper surface: Closest to but darker than RHS NN137A (Greyish Olive Green). Lower surface: Closest to but darker than RHS 147B (Moderate Yellow Green).

Flowers:

*Description*.—Solitary, zygomorphic.

*Type*.—Terminal raceme.

*Flowering habit*.—Freely flowering.

*Lastingness of individual flower on the plant*.—Approximately 7 to 10 days.

*Quantity per plant*.—Approximately 22.

*Quantity of fully open flowers per inflorescence*.—Approximately 9.

*Fragrance*.—Floral, crisp.

*Length*.—9.0 cm to 16.0 cm.

*Width*.—4.0 cm to 4.5 cm.

*Pedicel*.—Strength: Flexible. Aspect: Acute angle to stem. Length: Approximately 1.3 cm. Diameter: Approximately 1.0 mm. Texture: Glabrous. Color: RHS N144C (Strong Yellow Green).

Bud:

*Rate of opening*.—Generally, takes 3 to 4 days for bud to progress from first color to fully open flower.

*Quantity per inflorescence*.—Between 4 to 10 depending on inflorescence size.

*Bud just before opening*.—Shape: Globular. Length: Approximately 1.0 cm. Diameter: Approximately 1.0 cm. Color of both upper and lower surfaces: RHS NN155A (Yellowish White).

Corolla:

*Shape*.—Bilabiate.

*Aspect*.—Facing outward.

*Length*.—Approximately 2.6 cm.

*Width*.—Approximately 2.3 cm.

*Depth*.—Approximately 5.0 mm.

Petals:

*Quantity*.—5, petals are fused at base forming a throat and consisting of an upper lip with 2 petals and a lower lip with 3 petals, consisting of 2 lateral petals and one central petal.

*Shape*.—Obovate.

*Apex*.—Obtuse.

*Base*.—Fused.

*Margin*.—Slightly erose.

*Upper lip*.—Length of petals from throat: Approximately 9.0 mm. Width of each petal: Approximately 1.3 cm. Texture of both the upper and lower surfaces: Slightly pubescent. Gland color: Colorless; transparent. Color of both the upper and lower surfaces when fully open: Closest to RHS NN155D (White).

*Lower lip, lateral petals*.—Length of petals from throat: Approximately 8.0 mm. Width of each petal: Approximately 9.0 mm. Texture of both upper and lower surfaces: Slightly Pubescent. Gland color: Colorless, transparent. Color of both the upper and lower surfaces when fully open: Closest to RHS NN155D (White).

*Lower lip, central petal*.—Length from the palate: Approximately 8.0 mm. Width: Approximately 9.0 mm. Texture of both the upper and lower surfaces: Slightly pubescent. Gland color: Colorless, transparent. Color of both the upper and lower surfaces when fully open: Closest to RHS NN155D (White).

*Throat*.—Length: Approximately 11.0 mm. Width: Approximately 8.0 mm. Texture of inner and outer surfaces: Glabrous. Color of inner surface: RHS NN155D (White) with spots of RHS 144A (Strong Yellow Green). Color of outer surface: RHS NN155D (White) with spots of 144B (Strong Yellow Green). Palate color: RHS 144A (Strong Yellow Green). Palate texture: Sparsely pubescent. Teeth color: RHS 144C (Strong Yellow Green).

Calyx:

*Shape*.—Star, cupped.

*Diameter*.—Approximately 6.0 mm.

*Sepals*.—Quantity per flower: 5, fused. Shape: Lanceolate. Apex: Acute. Length: Approximately 3.0 mm. Width: Approximately 1.5 mm. Texture of both the upper and lower surfaces: Glabrous. Gland color: Colorless, transparent. Color of both the upper and lower surfaces: RHS 141A (Deep Yellowish Green).

Reproductive organs:

*Androecium*.—Stamen quantity: 4 per flower. Filament length: Approximately 4.0 mm. Filament texture: Glabrous. Gland color: Colorless, transparent. Filament color: RHS NN155D (White). Anther shape: Bi-lobed. Anther length: Approximately 1.0 mm. Anther color: RHS 154D (Light Yellow Green). Pollen amount: Abundant. Pollen color: RHS 155B (Yellowish White).

*Gynoecium*.—Pistil quantity: 1 per flower. Pistil length: Approximately 6.0 mm. Stigma shape: Globular. Stigma length: Approximately 1.0 mm. Stigma color: RHS N144C (Strong Yellow Green). Style length: Approximately 5.0 mm. Style color: RHS NN155D (White). Ovary diameter: Approximately 1.0 mm. Ovary texture: Glabrous. Ovary color: RHS 144B (Strong Yellow Green).

Seed: Not observed.

COMPARISON WITH PARENTAL LINES AND KNOWN VARIETY

When 'SAIANG001' is compared to both parental lines, the following differences can be found, as listed in Table 1:

TABLE 1

Comparison with Parental Lines

| Characteristic | 'SAIANG001' | Female Parent '5327-3' | Male Parent '5732-2' |
|---|---|---|---|
| Flower color | White | Light-purple | Light-pink |

When 'SAIANG001' is compared to the commercial comparison 'Balarcwite' (U.S. Plant Pat. No. 23,543), the following differences can be found, as listed in Table 2:

TABLE 2

Comparison with Similar Commercial Variety

| Characteristic | 'SAIANG001' | 'Balarcwite' |
|---|---|---|
| Plant habit | Upright | Semi-upright |
| Teeth color | RHS 144C (Strong Yellow Green) | RHS 145D (Light Yellowish Green) |
| Corolla size | Length: Approximately 2.6 cm Width: Approximately 2.3 cm Depth: Approximately 5.0 mm | Length: Approximately 3.1 cm. Width: Approximately 2.8 cm. Depth: Approximately 9.0 mm. |

I claim:

1. A new and distinct variety of *Angelonia* plant named 'SAIANG001' as described and illustrated herein.

* * * * *